United States Patent [19]

Lutz et al.

[11] 4,274,425
[45] Jun. 23, 1981

[54] MOUTHPIECE FOR A REDOX GAS MEASURING DEVICE

[75] Inventors: Dieter Lutz, Schweinfurt; Peter Krause, Schonungen; Axel Terveen; Volker Eibl, both of Munich, all of Fed. Rep. of Germany

[73] Assignee: Sachs-Systemtechnik GMbH, Schweinfurt, Fed. Rep. of Germany

[21] Appl. No.: 34,853

[22] Filed: Apr. 30, 1979

[30] Foreign Application Priority Data

May 12, 1978 [DE] Fed. Rep. of Germany ....... 2820916

[51] Int. Cl.$^3$ .............................................. A61B 5/08
[52] U.S. Cl. ..................................... 128/719; 128/730; 180/272; 23/232 E; 23/907; 422/84
[58] Field of Search ................... 128/203.11, 204.24, 128/206.22, 201.26, 201.28, 716, 717, 718, 724, 730, 719; 73/27 R, 421.5 R; 180/272; 23/232 E, 907

[56] References Cited

U.S. PATENT DOCUMENTS

| | | | |
|---|---|---|---|
| 2,591,691 | 4/1952 | Forrester | 422/84 |
| 3,124,124 | 3/1964 | Cross | 128/203.11 |
| 3,242,921 | 3/1966 | Seeler | 128/203.11 |
| 3,764,270 | 10/1973 | Collier et al. | 23/255 E |
| 3,853,477 | 12/1974 | Block et al. | 23/255 E |
| 3,957,046 | 5/1976 | Harris | 128/203.11 |
| 4,163,390 | 8/1979 | Rodder | 128/724 |

FOREIGN PATENT DOCUMENTS

1168529 10/1969 United Kingdom .
1283055 7/1972 United Kingdom .
1457290 12/1976 United Kingdom .

*Primary Examiner*—Robert W. Michell
*Assistant Examiner*—J. L. Kruter

[57] ABSTRACT

In a device for measuring redox gases, such as alcohol, in a person's breath, a disposable tubular mouthpiece forms an elongated flow passage and is displaceably securable in a measuring head. The mouthpiece has an opening at one end for blowing air into it and openings along its length for directing the air into the measuring head. A check valve is located in the flow passage so that air exhaled into the opening in the end of the mouthpiece can flow to the measuring head, but inhaling on the mouthpiece places the check valve in a closed position. The mouthpiece can be formed of a single molded piece or two tubular portions secured together. The end of the mouthpiece opposite the open end is closed and is spaced from the openings into the measuring head for forming a moisture chamber for collecting saliva.

20 Claims, 5 Drawing Figures

FIG. 3
FIG. 4
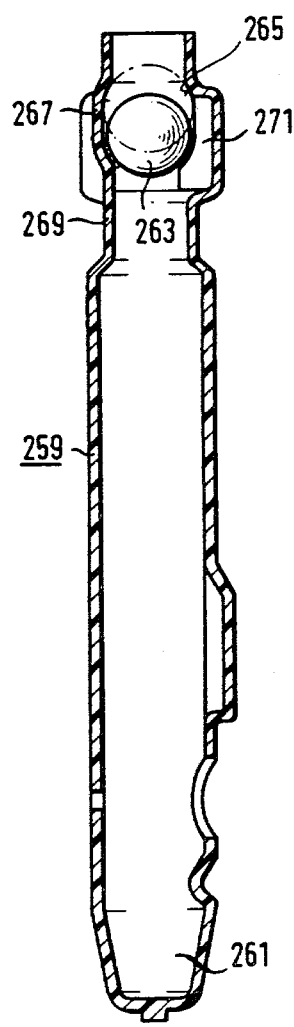
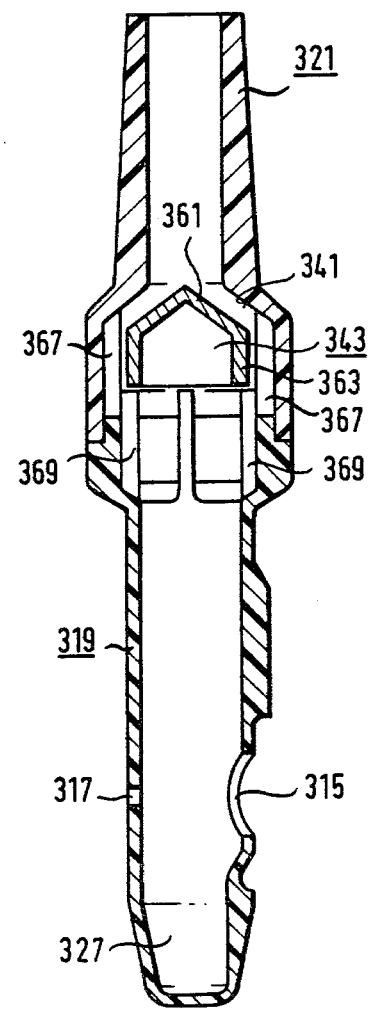

MOUTHPIECE FOR A REDOX GAS MEASURING DEVICE

SUMMARY OF THE INVENTION

The present invention is directed to a mouthpiece for the measuring head of a device which measures the concentration of redox gases, especially alcohol, in the breath of a person blown into the mouthpiece.

It is the primary object of the present invention to improve such a device which measures the concentration of redox gases, especially alcohol, in exhaled breath, and to assure that the device meets the proper health standards.

In accordance with the present invention, the mouthpiece is disposable and is releasably securable in the measuring head. A check valve is provided in the channel or passageway within the mouthpiece so that the passageway is closed if an attempt is made to inhale or suck on the mouthpiece. Accordingly, the mouthpiece can be replaced. The mouthpiece is formed as a disposable member and can be replaced after a measurement is taken. The check valve prevents drawing air back through the mouthpiece and prevents germs and other morbific agents located in the measuring head from being inhaled. The check valve can be a very simple structure. In particular, no special measures need be taken to prevent clogging of the check valve due to humidity, nicotine or tar deposits. From a health standard viewpoint as well as for reasons of operational security, it is preferred if the opposite end of the mouthpiece from the end into which breath is blown is closed and the openings from the passageway in the mouthpiece to the measuring head are spaced from the closed end so that the closed end portion of the mouthpiece forms a moisture chamber. The moisture chamber acts as a saliva trap preventing any saliva blown into the mouthpiece from reaching the measuring head and disturbing its measuring capability or interfering with the measured result.

To prevent any attempts at manipulating the breath for affecting the measured result, the check valve is preferably spaced at a distance from the open end of the mouthpiece. Accordingly, the valve body in the check valve cannot be displaced by a person's tongue. If necessary, the open end of the mouthpiece can be narrowed or covered by a grid or the like.

Since the mouthpiece is a disposable member, its structural design must be especially simple. Preferably, it is formed of molded pieces of plastics material. The check valve has proven to be especially useful when its valve body is symmetrical with respect to the axis of the flow passage through the mouthpiece and when the valve body can be freely moved between an annular shoulder serving as a valve seat and projections which hold the valve body but permit the flow of air through the mouthpiece. In this arrangement, the valve body does not have to be spring-biased into its open position. In use, it is sufficient if an annular shoulder within the mouthpiece closer to the open end thereof forms the valve seat against which the valve body effects a closing action. The influence of gravity on the valve body will cause it to move from the valve seat when the measuring device is being used.

Preferably, the mouthpiece is tubular in shape. It can be formed of two separate tubular portions which are joined together after the insertion of the valve body. To connect the tubular portions, complementary snap members can be provided on their adjacent end sections. Further, the tube portions can be joined together by a bonding action or by welding, in particular ultrasonic welding. Projections for supporting the valve body when air is being breathed into the mouthpiece, can be provided on one or both of the two portions. In one preferred embodiment the projections can be provided on a ring secured between shoulders on each of the tube portions.

In another embodiment, the mouthpiece is produced as a blow formed single molded piece of plastics material. The opening into the flow passage in the mouthpiece is provided with a diameter only slightly smaller than the diameter of the valve body, so that the valve body can be pressed into position in the mouthpiece through the open end.

The valve body can be constructed as a sphere, a cone, a truncated cone or as a paraboloid. The valve body can be constructed asymmetrically in the axial direction of the flow passage in the mouthpiece, since such a valve body can be produced as a hollow member open in the direction facing away from the valve seat.

In assembling the device, it is preferable to insert the mouthpiece into the measuring head in the direction of its flow passage axis. A projection or nose is formed on the outer surface of the mouthpiece and aligns with a complementary shaped opening in the measuring head to assure proper alignment of the mouthpiece in the measuring head.

To avoid any mutual influence of the separate measuring sensors in the measuring head, each sensor is arranged in a different channel. The mouthpiece has outlet openings disposed transversely of the axial direction of the mouthpiece and these openings align with the channels containing the sensors. The outlet openings from the mouthpiece are dimensioned in accordance with the purpose of the measurement to be affected by each sensor. In particular, the outlet opening, through which exhaled air is supplied to the alcohol concentration measuring sensor, is dimensioned so that any cooling effect which would lead to a measuring error is prevented. Though the opening into its channel is made small, the cross-section of the channel containing the alcohol measuring sensor can still be sufficiently large so that it is adequately ventilated through the mouthpiece connection opening, when the mouthpiece is removed.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWING

In the drawing:

FIGS. 2 to 4 are cross-sectional views of three embodiments of the mouthpiece which could be used in the measuring head illustrated in FIG. 1.

DETAIL DESCRIPTION OF THE INVENTION

Figures 1, 1A:
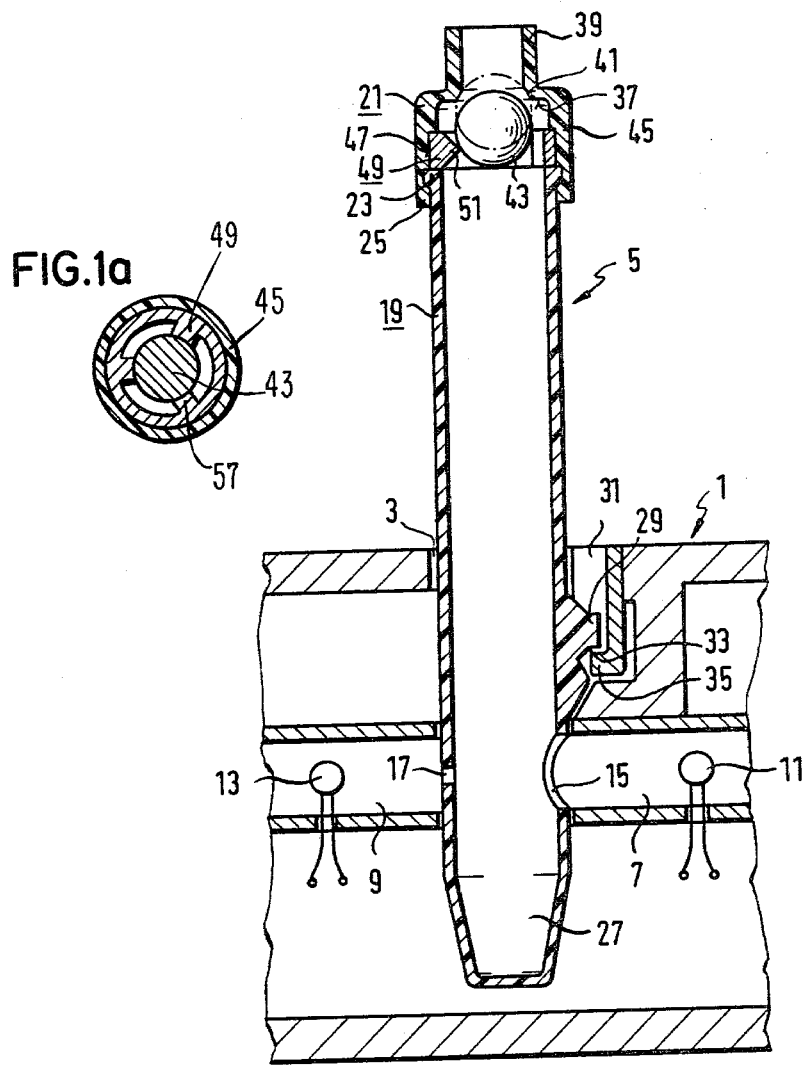
FIG. 1 is a cross-sectional view of one embodiment of a device illustrating a mouthpiece inserted into a measuring head.
FIG. 1a is a cross-section of a portion of the mouthpiece shown in FIG. 1.

In FIG. 1 a measuring head 1 is shown having an insertion opening 3 into which an axially elongated tubular mouthpiece 5 is inserted. Within the measuring head 1, two channels 7 and 9 extend normal to the axis of the mouthpiece 5. A sensor 11, 13 is provided in each channel 7, 9. The sensors 11, 13 form part of a device, not shown in detail, for measuring the concentration of alcohol in a person's breath. In channel 7, the sensor 11 detects the direction of flow and/or throughput of air breathed into the mouthpiece and passing through the opening 15 into the channel. In the other channel 9, sensor 13 determines the concentration of alcohol in the air flowing from the passage in the mouthpiece 5 through the opening 17 into the channel. The opposite ends of the channels 7 and 9 from the openings 15, 17 are open. While opening 15 has a cross-section corresponding to the passageway in the channel 7, opening 17 is much smaller in cross-section than channel 7 so that the flow velocity of air into the channel is kept low, and to prevent any cooling effect which might result in measuring errors. The sensor 13 is a semiconductor. When the mouthpiece 5 is removed from the insertion opening 3 in the measuring head 1, channels 7, 9 are vented through the insertion opening 3.

Mouthpiece 5 is formed of two axially extending tubular portions 19, 21. Each tubular portion is made as a molded piece of plastics material. The tube portions are in axial alignment and are interconnected at their telescoping ends by complementary snap members 23, 25. Tube portion 19 is insertable into the measuring head 1 and its end within the measuring head is spaced axially from the outlet openings 15, 17. Accordingly, a moisture chamber 27 is formed at the closed end of tubular portion 19 in which saliva blown into the mouthpiece can be collected. This arrangement prevents saliva from reaching the interior of the measuring head 1 and, in particular, the sensors 11, 13.

On the outer surface of the tubular portion 19, intermediate the openings 15, 17 and the end connected to the tubular portion 21, a projection 29 is provided which fits into a groove 31 formed in the insertion opening 3 of the measuring head. The groove 31 extends in the axial or inserting direction of the mouthpiece 5. The interengagement of the projection 29 within the groove 31 assures the proper orientation of the mouthpiece 5 within the measuring head 1. Below the projection 29 as viewed in FIG. 1, a locking recess 33 is provided which cooperates with a flexible locking cam 35 on the measuring head and fixes the mouthpiece 5 in the axial direction within the measuring head 1.

The upper end of the tubular portion 21 forms an opening through which a person's breath can be directed into the mouthpiece 5. Upper tubular portion 21, from the open end, consists of a cylindrical section 39, a radially outwardly extending shoulder 37 and another cylindrical section 45 extending axially from the radially outer part of the shoulder. The inner edge of shoulder 37 forms a valve seat 41 for a check valve having a spherical valve body 43. In the wider cylindrical section 45 of tube portion 21, and spaced axially from the annular shoulder 37, a ring 49 extends around the surface of the passageway through the mouthpiece and is held in position between the upper end of tubular portion 19 and a shoulder formed by a recess 47 in the inner surface of cylindrical section 45. The inner diameter of the ring 49 is greater than the diameter of the valve body 43.

Nose-like projections 51 extend radially inwardly from the inner surface of the ring 49 and are spaced apart around the inner circumference of the ring note the cross-section of the ring 49 shown in FIG. 1a. The nose-like projections 51 extend inwardly beyond the outside diameter of the valve body 43 and provide supports so that the valve body is prevented from continuing its passage downwardly through the tubular portion 19. Air blown into the upper open end of the mouthpiece 5 passes downwardly through tubular portion 21 around the valve body 43 and through the spaces between adjacent projections 51 into the passageway through the tubular portion 19. The check valve prevents any inhaling or suction action on the mouthpiece so that germs and the like cannot be inhaled through the mouthpiece 5 from the measuring head 1. Any suction action causes the valve body 43 to move into contact with the valve seat 41 and close off any flow to the open end of the mouthpiece. The diameter and axial length of the cylindrical section 39 of tubular portion 21 has been chosen so that the valve body 43 cannot be displaced away from the valve seat 41 by the tongue of a person using the mouthpiece.

Figure 2:
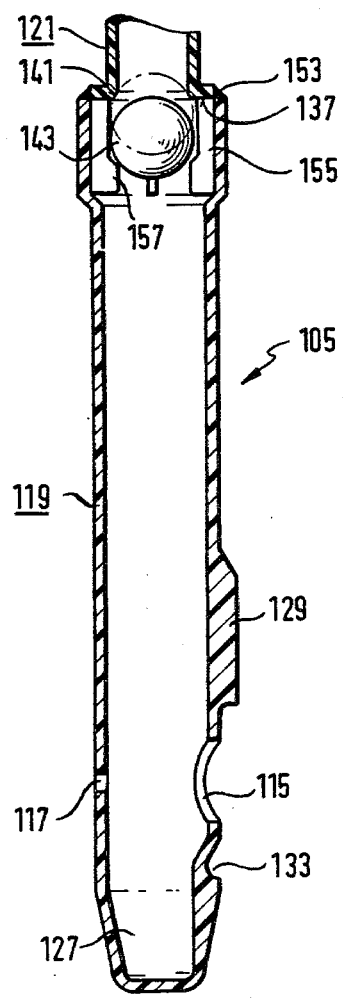

FIG. 2 illustrates another embodiment of a mouthpiece 105. Parts of the mouthpiece similar to those in FIG. 1 are identified by the same reference numerals, however, with the addition of a prefix 10 or 1. This mouthpiece 105 operates in the same manner as the mouthpiece displayed in FIG. 1.

Mouthpiece 105, illustrated in FIG. 2, is a tubular member having a pair of outlet openings 115, 117 spaced closely from its closed lower end. When the mouthpiece is inserted into the measuring head, the outlet openings 115, 117 open into the channels in the measuring head. Mouthpiece 105 includes two tubular portions 119, 121 which, in contrast the embodiment shown in FIG. 1, are not connected by snap members, but are ultrasonically welded together by weld deposit 153 at their adjacent end faces. The lower closed end section of the tubular portion 119 below the outlet openings 115, 117 forms a moisture chamber 127. For the proper orientation of the mouthpiece 105 when it is inserted into the measuring head, a nose-like projection 129 is provided on its outer surface which extends into a groove formed into the measuring head. Below opening 115, a locking recess 133 is formed in the outer surface of the mouthpiece so that it can interfit with a cam or similar member on the measuring head. Unlike the embodiment in FIG. 1, the projection 129 and the locking recess 133 are located on opposite sides of the opening 115.

The lower end of tubular portion 121 in combination with the upper end section of tubular portion 119 forms a check valve. The tubular portion 121 has a cylindrical section terminating at its lower end face which extends transversely outwardly from the cylindrical section forming a ring shoulder 137. The upper end section of the tubular portion 119 has a larger diameter as compared to the cylindrical section of the tubular portion 121 and its inner surface is in juxtaposition to the radially outer edge of the ring shoulder 137. The weld deposit 153 is formed between the end face of the tubular portion 19 and the outer edge of the ring shoulder 137. The radially inner edge of ring shoulder 137 forms a valve seat 141. Connected to and extending axially downwardly from the ring shoulder 137 are a plurality of vanes 155. The vanes 155 are spaced apart around the circumferential inner surface at the upper end section of the tubular portion 119. The vanes 155 are located in axial sectional planes of the tubular portion 119. The lower ends of the vanes 155 form inwardly directed projections 157 and afford supports for a spherically shaped valve body when it is in its lower position. The spherical valve body 143 is freely movable between the valve seat 141 and the support projections 157. The vanes 155 are formed integrally with and extend downwardly from the tubular portion 121 with the vanes fitting into the upper end section of the tubular portion 119.

In FIG. 3 a mouthpiece is illustrated which is molded from a single piece of a plastics material hose or tube into a shaped tubular body 259. The arrangement of the outlet openings, locking projections and locking recesses are similar to those disclosed in the embodiments shown in FIGS. 1 and 2. At its lower end, the tube body 259 is bent inwardly forming a closure so that its lower end below the openings afford a moisture chamber 261. Adjacent its upper end, the tube body 259 forms a check valve. The check valve includes a spherical valve body 263 which can fit against a valve seat 265 to prevent the suction of air upwardly through the passage in the mouthpiece and out of its open end. At its upper end, the tube body 259 has a reduced diameter tube section 269 as compared to the section forming the lower part of the tube body and an intermediate portion of this tube section is expanded outwardly forming an annular expanded section 267. The spherical valve body 263 is positioned within the expansion section 267. The inside diameter of the section 269 is selected so that the spherical valve body 263 can be inserted through the open end into the expanded section 267 due to the elasticity of the material forming the tube body. Circumferentially spaced and axially extending parts of the expanded section 267 are directed radially inwardly and form ribs. The space between the ribs within the expanded section 267 form passageways 271 for the flow of air around the valve body 63 when the valve body is in its lower position supported on the ribs. The inner edges of the ribs form guides for the valve body 63 so that it is freely movable within the expanded section 267 with relatively little play.

In FIG. 4, a mouthpiece is illustrated which differs from the embodiment in FIG. 2 in the general arrangement of its check valve. The general arrangement and function of the mouthpiece is similar to that disclosed with regard to FIGS. 1 and 2. In FIG. 4 reference numerals similar to those in FIG. 1 are used, however, with the prefix 30 or 3. The mouthpiece is formed of two axially extending tubular portions 319, 321 connected to one another at their juxtaposed end faces. Tubular portion 319 has openings 315, 317 for supplying air into the measuring head and a moisture chamber 327 at the lower closed end of the tubular portion. At the lower part of tubular portion 321, its walls are expanded outwardly and a frusto-conically shaped section of the walls form a valve seat 341. Valve body 343 located within the expanded section of the tubular portion 321 fits against the valve seat 341 in its upper position. Valve body 343 has a conically shaped top 361 which is complementary to the frusto-conical surface forming the valve seat 341. Below its conically shaped top 361, the valve body has a hollow cylindrically shaped guide section 363. Valve body 343 is freely movable within the expanded section of tubular portion 321 between the valve seat 341 and the adjacent end of the tubular portion 319. Within this space, the valve body is guided in the axial direction by axially extending guide ribs 367 formed on and extending inwardly from the inner surface of the expanded section of the tubular portion 321. Ribs 367 guide the hollow cylindrical section 363 of the valve body and prevent any tilting of the axis of the conically shaped top 361 relative to the axis of the valve seat 341. Within the upper section of the tubular portion 319, ribs 369 extend inwardly into the flow passage through the mouthpiece below the valve body 341 and limit the downward movement of the valve body. Accordingly, the valve body is freely movable between the valve seat 341 and the upper ends of the ribs 369.

While specific embodiments of the invention have been shown and described in detail to illustrate the application of the inventive principles, it will be understood that the invention may be embodied otherwise without departing from such principles.

What is claimed is:

1. Mouthpiece for a device for measuring the concentration of redox gases, especially alcohol, in exhaled air, comprising an axially elongated tubular member forming an axially extending passageway and having a first end forming an opening through which air is exhaled into the passageway and a second end, means formed on the outside surface of said tubular member for releasably securing said tubular member to the measuring device, valve means in combination with said tubular member forming a check valve within the passageway in said tubular member for permitting the flow of exhaled air from the first end toward the second end past said check valve while preventing an induced flow of air through the passageway around the check valve to the first end, said tubular member being closed at the second end thereof and having at least one outlet opening therefrom intermediate and spaced from said check valve and the second end of said tubular member, and the passageway in said tubular member between said outlet opening and the second end thereof forming a moisture chamber for collecting saliva at a location within said passageway downstream of the location of said outlet opening where the flow of exhaled air can enter the measuring device, and after use said mouthpiece being removable from the measuring device and being disposable.

2. Mouthpiece, as set forth in claim 1, wherein said valve means comprises a valve body located within the passageway in said tubular member and being symmetrical relative to the axis of said tubular member, said check valve including a valve seat formed by an annular part of said tubular member, circumferentially spaced supports located in said tubular member and spaced more remotely from the first end thereof than said valve seat and said supports extending into the passageway through said tubular member, and said valve body being displaceable within the passageway in said tubular member between said valve seat and said supports so that air flow is blocked when said valve body is in contact with said valve seat and air can flow when said valve body contacts said supports.

3. Mouthpiece, as set forth in claim 2, wherein said tubular member comprises a first tubular portion and a second tubular portion in coaxial alignment with and extending axially from said first tubular portion, said first tubular portion forming the first end of said tubular member and said valve seat, and said second tubular portion forming the second end of said tubular member and having said at least one outlet opening spaced from the second end and from the opposite end of said second tubular portion.

4. Mouthpiece, as set forth in claim 3, wherein said second tubular portion has a first end and a second end which forms the second end of said tubular member, a ring member mounted within said tubular member and supported on the first end of said second tubular member and extending therefrom into said first tubular member toward and spaced from said valve seat on the opposite side of said valve seat from the first end of said tubular body, and projections secured to and extending radially inwardly from said ring, said projections spaced apart in the circumferential direction around the inside surface of said ring, and said projections forming said supports for said valve body.

5. Mouthpiece, as set forth in claim 3, wherein said first tubular portion has a first end forming the first end of said tubular member and a second end forming said valve seat, the second end of said first tubular section defining a ring shoulder extending around and outwardly from said valve seat, axially extending segments secured to and extending in the axial direction of said tubular member from said ring shoulder toward the second end of said tubular member, said segments spaced apart in the circumferential direction of said tubular member and the ends of said segments spaced from said ring shoulder projecting inwardly into the passageway through said tubular member and forming said supports for said valve body.

6. Mouthpiece, as set forth in claim 3, wherein said first tubular portion has a first end forming the first end of said tubular member and a second end, said second tubular portion has a first end and a second end forming the second end of said tubular member, the second end of said first tubular portion encircling the first end of said second tubular portion, and complementary snap members formed on the inner surface of said first tubular portion adjacent the second end thereof and on the outer surface of said second tubular portion adjacent the first end thereof for securing said first and second tubular portions together.

7. Mouthpiece, as set forth in claim 3, wherein said first tubular portion has a first end forming the first end of said tubular member and a second end, said second tubular portion has a first end and a second end forming the second end of said tubular member, the second end of said first tubular portion and the first end of said second tubular portion being in juxtaposed relation and being secured together.

8. Mouthpiece, as set forth in claim 7, wherein the second end of said first tubular portion being weld connected to the first end of said second tubular portion.

9. Mouthpiece, as set forth in claim 2, wherein said tubular member comprises an axially elongated length of a tube of plastics material molded in one piece.

10. Mouthpiece, as set forth in claim 2, wherein said valve body has a spherical shape.

11. Mouthpiece, as set forth in claim 2, wherein said valve body has a conical shape.

12. Mouthiece, as set forth in claim 2, wherein said valve body has a frusto-conical shape.

13. Mouthpiece, as set forth in claim 2, wherein said valve body has a paraboloid shape.

14. Mouthpiece, as set forth in claim 2, wherein said valve body is a hollow member.

15. Mouthpiece, as set forth in claim 2, wherein the annular portion of said tubular member forming said valve seat is frusto-conically shaped and the part of said valve body which contacts the valve seat has a complementary frusto-conical shape.

16. Mouthpiece, as set forth in claim 2, wherein said check valve is spaced axially from the first end of said tubular member a sufficient distance adapted to prevent contact between said valve body and the tongue of a person using the mouthpiece.

17. Device for measuring the concentration of redox gases, especially alcohol, in exhaled air, comprising a measuring head having an opening therein, an axially elongated tubular member forming an axially extending passageway having a first end forming an opening through which air is exhaled into the passageway and a second end, an axially extending part of said tubular member extending from said second end toward said first end being fitted into the opening in said measuring head, said axially extending part having an opening therein spaced from said second end for admitting exhaled air into said measuring head, said second end being closed and the portion of said axially extending part between said opening and said second end forming a moisture chamber for collecting saliva, means on the outer surface of said tubular member for releasably securing said tubular member within the opening in said measuring head, and valve means in combination with said tubular member and located between said first end and said opening for forming a check valve within the passageway in said tubular member for permitting the flow of exhaled air from the first end toward the second end through said check valve while preventing an induced flow of air through the passageway around said check valve to the first end.

18. Device, as set forth in claim 17, wherein said measuring head has at least two separate channels extending transversely of said tubular member, a sensor within each said channel, and said tubular member having at least two said openings therefrom each arranged to open into a different one of said separate channels.

19. Device, as set forth in claim 18, wherein at least one of said channels has a transverse cross-sectional area larger than the diameter of the opening in said tubular member opening into said channel.

20. Device, as set forth in claim 18, wherein said means for releasably securing said tubular member comprises a projection extending outwardly from the outer surface of said tubular member, the opening in said measuring head having a groove extending in the direction of insertion of said tubular member into said measuring head and having a shape complementary to said projection so that the insertion of said projection into said groove effects a positive alignment of the openings in said tubular member with the channels in said measuring head.

* * * * *